(12) United States Patent
Ono et al.

(10) Patent No.: US 10,087,449 B2
(45) Date of Patent: Oct. 2, 2018

(54) PHARMACEUTICAL COMPOSITION FOR TREATING CHRONIC KIDNEY DISEASE

(71) Applicants: SHIONOGI & CO., LTD., Osaka-shi, Osaka (JP); KEIO UNIVERSITY, Tokyo (JP)

(72) Inventors: Takashi Ono, Toyonaka (JP); Katsutoshi Yamada, Toyonaka (JP); Norito Yoshimura, Toyonaka (JP); Toshihiro Shinosaki, Toyonaka (JP); Yoshinari Gahara, Toyonaka (JP); Hiroshi Itoh, Tokyo (JP); Shu Wakino, Tokyo (JP); Takeshi Kanda, Tokyo (JP); Kazuhiro Hasegawa, Tokyo (JP); Motoaki Komatsu, Tokyo (JP)

(73) Assignees: SHIONOGI & CO., LTD., Osaka-shi (JP); KEIO UNIVERSITY, Tokyo (JP)

( * ) Notice: Subject to any disclaimer, the term of this patent is extended or adjusted under 35 U.S.C. 154(b) by 0 days.

(21) Appl. No.: 15/302,280

(22) PCT Filed: Apr. 6, 2015

(86) PCT No.: PCT/JP2015/060696
§ 371 (c)(1),
(2) Date: Oct. 6, 2016

(87) PCT Pub. No.: WO2015/156237
PCT Pub. Date: Oct. 15, 2015

(65) Prior Publication Data
US 2017/0107521 A1 Apr. 20, 2017

(30) Foreign Application Priority Data
Apr. 7, 2014 (JP) ................. 2014-078480

(51) Int. Cl.
*A61K 48/00* (2006.01)
*C12N 15/113* (2010.01)
*C12Q 1/48* (2006.01)

(52) U.S. Cl.
CPC .......... *C12N 15/1137* (2013.01); *C12Q 1/48* (2013.01); *C12Y 201/01001* (2013.01); *C12N 2310/11* (2013.01); *C12N 2310/14* (2013.01); *G01N 2333/91017* (2013.01); *G01N 2500/04* (2013.01)

(58) Field of Classification Search
CPC ..................................... A61K 48/00

USPC ............................................. 514/44
See application file for complete search history.

(56) References Cited

U.S. PATENT DOCUMENTS
2013/0243790 A1    9/2013    Kahn et al.

FOREIGN PATENT DOCUMENTS
WO    WO 2004/071267 A2    8/2004
WO    WO 2012/068463 A2    5/2012
WO    WO 2012/123299 A1    9/2012

OTHER PUBLICATIONS

English translation of International Preliminary Report on Patentability and Written Opinion dated Oct. 20, 2016, in PCT International Application No. PCT/JP2015/060696.
International Search Report (PCT/ISA/210) issued in PCT/JP2015/060696, dated May 19, 2015.
Kim et al., "Composite Three-Marker Assay for Early Detection of Kidney Cancer", Cancer Epidemiology, Biomarkers, and Prevention, vol. 22, No. 3, Mar. 2013, pp. 390-398.
Komatsu et al., "Nicotinamide-N-methyltransferase (NNMT) is one of the factor of cardio-renal interaction by elevating homocysteine level", Folia endocrinologica Japonica, vol. 89, No. 2, Sep. 2013, p. 758.
Nagai et al., "Effects of Nicotinamide and Niacin on Bleomycin-Induced Acute Injury and Subsequent Fibrosis in Hamster Lungs", Experimental Lung Research, vol. 20, 1994, pp. 263-281.
Tang et al., "Nicotinamide N-methyltransferase induces cellular invasion through activating matrix metalloproteinase-2 expression in clear cell renal cell carcinoma cells", Carcinogenesis, vol. 32, No. 2, 2010, pp. 138-145.
Traister et al., "Nicotinamide induces apoptosis and reduces collagen I and pro-inflammatory cytokines expression in rat hepatic stellate cells", Scandinavian Journal of Gastroenterology, vol. 40, 2005, pp. 1226-1234.
Written Opinion (PCT/ISA/237) issued in PCT/JP2015/060696, dated May 19, 2015.

*Primary Examiner* — Kimberly Chong
(74) *Attorney, Agent, or Firm* — Birch, Stewat, Kolasch & Birch, LLP (57) ABSTRACT

This invention is related to a therapeutic agent for treating chronic kidney disease comprising a substance which inhibits the enzymatic activity of NNMT or suppresses NNMT gene expression, or a method for screening a therapeutic agent for treating chronic kidney disease which targets the NNMT enzyme or NNMT gene.

3 Claims, 5 Drawing Sheets

Specification includes a Sequence Listing.

SEQUENCE LISTING

```
<160> NUMBER OF SEQ ID NOS: 5

<210> SEQ ID NO 1
<211> LENGTH: 264
<212> TYPE: PRT
<213> ORGANISM: Homo sapiens

<400> SEQUENCE: 1

Met Glu Ser Gly Phe Thr Ser Lys Asp Thr Tyr Leu Ser His Phe Asn
1               5                   10                  15
```

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
    50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95

Trp Leu Lys Lys Glu Pro Glu Ala Phe Asp Trp Ser Pro Val Val Thr
            100                 105                 110

Tyr Val Cys Asp Leu Glu Gly Asn Arg Val Lys Gly Pro Glu Lys Glu
            115                 120                 125

Glu Lys Leu Arg Gln Ala Val Lys Gln Val Leu Lys Cys Asp Val Thr
        130                 135                 140

Gln Ser Gln Pro Leu Gly Ala Val Pro Leu Pro Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
            260

<210> SEQ ID NO 2
<211> LENGTH: 25
<212> TYPE: RNA
<213> ORGANISM: Artificial Sequence
<220> FEATURE:
<223> OTHER INFORMATION: Synthetic

<400> SEQUENCE: 2
ccacauccaa uaaugaagga cucuu                                        25

<210> SEQ ID NO 3
<211> LENGTH: 25
<212> TYPE: RNA
<213> ORGANISM: Artificial Sequence
<220> FEATURE:
<223> OTHER INFORMATION: Synthetic

<400> SEQUENCE: 3
aagaguccuu cauuauugga ugugg                                        25

<210> SEQ ID NO 4
<211> LENGTH: 14
<212> TYPE: DNA
<213> ORGANISM: Artificial Sequence
<220> FEATURE:
<223> OTHER INFORMATION: Synthetic

```
<400> SEQUENCE: 4
cacagtgtct ggac                                                    14

<210> SEQ ID NO 5
<211> LENGTH: 14
<212> TYPE: DNA
<213> ORGANISM: Artificial Sequence
<220> FEATURE:
<223> OTHER INFORMATION: Synthetic

<400> SEQUENCE: 5
gtggtagaag agta                                                    14
```

PHARMACEUTICAL COMPOSITION FOR TREATING CHRONIC KIDNEY DISEASE

REFERENCE TO SEQUENCE LISTING SUBMITTED VIA EFS-WEB

This application includes an electronically submitted sequence listing in .txt format. The .txt file contains a sequence listing entitled "2016 Dec. 21 0032-0327PUS1 ST25.txt" created on Dec. 21, 2016 and is 3,418 bytes in size. The sequence listing contained in this .txt file is part of the specification and is hereby incorporated by reference herein in its entirety.

The present invention relates to a pharmaceutical composition for treating chronic kidney disease, comprising a substance inhibiting the enzymatic activity of a specific protein or suppressing a specific gene. More specifically, the invention relates to a pharmaceutical composition for treating chronic kidney disease, comprising a substance inhibiting the enzymatic activity of nicotinamide N-methyltransferase (hereinafter, referred to NNMT) or suppressing NNMT gene expression, or a method for screening a substance for treating chronic kidney disease with the enzymatic activity of NNMT or NNMT gene expression.

BACKGROUND ART

Patients with renal dysfunction have been increasing worldwide and the increased number of patients with end-stage kidney disease undergoing artificial dialysis has become a medical economic problem. In recent years, the concept of disease named chronic kidney disease (CKD) has been proposed, resulting in growing the recognition for the importance of the prevention and treatment. Chronic kidney disease means the state in which "the observation of renal disease with positive proteinuria" or "reduced renal function (glomerular filtration rate less than 60 ml/min/1.73 $m^2$)" continues over three months.

Hypertension, diabetes, dyslipidemia and smoking become risk factors for the onset and progression of chronic kidney disease and the growing number of patients in the future is feared by the spread of metabolic syndrome due to a change in life style. Chronic kidney disease is not only the risk of progression to end-stage kidney disease but also the risk factor for cardiovascular events and has become causes of myocardial infarction, heart failure, cerebral infarction and death.

For the prevention and treatment of chronic kidney disease, in addition to the life guidance and dietary advice, the treatment by antihypertensive therapy using angiotensin receptor antagonist and calcium antagonist is carried out. But more effective prophylactic and therapeutic agents for renal dysfunction are needed, because the existing therapies are not effective enough.

The pathological features in chronic kidney disease are glomerulosclerosis and tubulointerstitial fibrosis. The pathology image at end-stage renal disease is remarkable for the shedding and fibrosis of parenchymal cells. It is known that renal dysfunction progresses more rapidly in patient with than without tubulointerstitial fibrosis among patient with chronic kidney disease.

Fibrosis can occur in every tissue, while it can be progressed by common mechanisms, irrespective of the kind of trigger of its development. On the other hand, the construction of tissue and organ in animal is maintained by the fibers including collagen. When tissue receives any damage, the damaged tissue is restored to the original tissue in process of wound healing accompanied by collagen production. However, when tissue receives immunological, chemical, mechanical, metabolic or other damage several times and the degree of their damages is large, the accumulation of excess fibrous connective tissue can occur. The accumulation of such connective tissue is irreversible and the abnormal increase of fiber causes fibrotic disease in which tissues and organs are not able to function normally.

Since there is no effective agent for chronic kidney disease, particularly chronic kidney disease with fibrosis, the identification of novel enhancing factor for fibrosis that has potential for drug target is desired.

PRIOR ART REFERENCE

Non-Patent Literature

Non-patent literature 1: CKD clinical practice guide 2009, Japan Society of Nephrology editing

SUMMARY OF THE INVENTION

An objection of the present invention is providing a pharmaceutical composition for treating chronic kidney disease, especially chronic kidney disease by inhibiting the enzymatic activity of NNMT or suppressing NNMT gene expression.

Problem to be Solved by the Invention

The present inventors found that NNMT gene expression which encoded the enzyme of nicotinic acid metabolism was upregulated in the kidney by exploring a molecule that varied in accordance with nephropathy induced in the animal model of chronic kidney disease, and completed the present invention.

Namely, the present invention provides below [1] to [34]:

[1] A pharmaceutical composition for treating chronic kidney disease, comprising a substance inhibiting the enzymatic activity of NNMT or suppressing NNMT gene expression.

[2] The composition of [1], wherein the substance inhibiting the enzymatic activity of NNMT or suppressing NNMT gene expression is a nucleic acid.

[3] The composition of [2], wherein the nucleic acid is a siRNA or an antisense oligonucleotide or an expression vector thereof.

[4] The composition of [1], wherein the substance inhibiting the enzymatic activity of NNMT is an antibody.

[5] A method for screening a substance for treating chronic kidney disease, wherein the enzymatic activity of NNMT or NNMT gene expression is used as an indicator.

[6] A pharmaceutical composition for treating chronic kidney disease with fibrosis, comprising a substance inhibiting the enzymatic activity of NNMT or suppressing NNMT gene expression.

[7] The composition of [6], wherein the substance inhibiting the enzymatic activity of NNMT or suppressing NNMT gene expression is a nucleic acid.

[8] The composition of [7], wherein the nucleic acid is a siRNA or an antisense oligonucleotide or an expression vector thereof.

[9] The composition of [6], wherein the substance inhibiting the enzymatic activity of NNMT is an antibody.

[10] A method for screening a substance for treating chronic kidney disease with fibrosis, wherein the enzymatic activity of NNMT or NNMT gene expression is used as an indicator.

[11] A method for treating chronic kidney disease, comprising a step of administering to a substance inhibiting the enzymatic activity of NNMT or suppressing NNMT gene expression.

[12] The method of [11], wherein the substance inhibiting the enzymatic activity of NNMT or suppressing NNMT gene expression is a nucleic acid.

[13] The method of [12], wherein the nucleic acid is a siRNA or an antisense oligonucleotide or an expression vector thereof.

[14] The method of [11], wherein the substance inhibiting the enzymatic activity of NNMT is an antibody.

[15] A method for treating chronic kidney disease with fibrosis, comprising a step of administering a substance inhibiting the enzymatic activity of NNMT or suppressing NNMT gene expression.

[16] The method of [15], wherein the substance inhibiting the enzymatic activity of NNMT or suppressing NNMT gene expression is a nucleic acid.

[17] The method of [16], wherein the nucleic acid is a siRNA or an antisense oligonucleotide or an expression vector thereof.

[18] The method of [15], wherein the substance inhibiting the enzymatic activity of NNMT is an antibody.

[19] A substance inhibiting the enzymatic activity of NNMT or suppressing NNMT gene expression for treating chronic kidney disease.

[20] A nucleic acid inhibiting the enzymatic activity of NNMT or suppressing NNMT gene expression for treating chronic kidney disease.

[21] A siRNA or an antisense oligonucleotide or an expression vector thereof suppressing NNMT gene expression for treating chronic kidney disease.

[22] An antibody inhibiting the enzymatic activity of NNMT for treating chronic kidney disease.

[23] A substance inhibiting the enzymatic activity of NNMT or suppressing NNMT gene expression for treating chronic kidney disease with fibrosis.

[24] A nucleic acid inhibiting the enzymatic activity of NNMT or suppressing NNMT gene expression for treating chronic kidney disease with fibrosis.

[25] A siRNA or an antisense oligonucleotide or an expression vector thereof suppressing NNMT gene expression for treating chronic kidney disease with fibrosis.

[26] An antibody inhibiting the enzymatic activity of NNMT for treating chronic kidney disease with fibrosis.

[27] A use of a substance inhibiting the enzymatic activity of NNMT or suppressing NNMT gene expression for the production of therapeutic agent for treating chronic kidney disease.

[28] A use of a nucleic acid inhibiting the enzymatic activity of NNMT or suppressing NNMT gene expression for the production of therapeutic agent for treating chronic kidney disease.

[29] A use of a siRNA or an antisense oligonucleotide or an expression vector thereof suppressing NNMT gene expression for the production of therapeutic agent for treating chronic kidney disease.

[30] A use of an antibody inhibiting the enzymatic activity of NNMT for the production of therapeutic agent for treating chronic kidney disease.

[31] A use of a substance inhibiting the enzymatic activity of NNMT or suppressing NNMT gene expression for the production of therapeutic agent for treating chronic kidney disease with fibrosis.

[32] A use of a nucleic acid inhibiting the enzymatic activity of NNMT or suppressing NNMT gene expression for the production of therapeutic agent for treating chronic kidney disease with fibrosis.

[33] A use of a siRNA or an antisense oligonucleotide or an expression vector thereof suppressing NNMT gene expression for the production of therapeutic agent for treating chronic kidney disease with fibrosis.

[34] A use of an antibody inhibiting the enzymatic activity of NNMT for the production of therapeutic agent for treating chronic kidney disease with fibrosis.

Effect of the Invention

According to the present invention, the expression of protein or gene of Collagen type I alpha 1 (hereinafter, referred to COL1A1) or Collagen type III alpha 1 (hereinafter, referred to COL3A1) or Collagen type IV alpha 1 (hereinafter, referred to COL4A1) may be inhibited by inhibiting the enzymatic activity of NNMT or suppressing NNMT gene expression, and a substance inhibiting the enzymatic activity of NNMT or suppressing NNMT gene expression is used as an active ingredient of a pharmaceutical composition for treating chronic kidney disease. The pharmaceutical composition of the present invention provides a therapeutic agent having new mechanism of action and a therapeutic agent inhibiting the enzymatic activity of the specific protein or suppressing the specific gene expression, and is characterized by having less toxicity compared with traditional agent for treating chronic kidney disease. And the present invention provides a method for screening a therapeutic agent for treating chronic kidney disease which targets NNMT enzyme or NNMT gene.

Mode for Carrying out the Invention

A term in this specification, unless specifically referred to, is used as the meaning commonly used in the art.

The present invention provides a pharmaceutical composition for treating chronic kidney disease especially for treating chronic kidney disease with fibrosis, comprising a substance inhibiting the enzymatic activity of NNMT or suppressing NNMT gene expression.

Chronic kidney disease means the state in which the observation of renal disease with positive proteinuria or reduced renal function (glomerular filtration rate less than 60 ml/min/1.73 m$^2$) continues over three months, and chronic kidney disease includes chronic renal failure, chronic nephritis, tubulointerstitial failure, nephrotic syndrome, polycystic kidney disease, diabetic nephropathy, and renal sclerosis, etc.

Chronic kidney disease with fibrosis means chronic kidney disease displaying signs of fibrosis in glomerulosclerosis and tubulointerstitial etc.

We identified NNMT as a new target molecule of chronic kidney disease as described example 1-5 in this specification.

In this specification, "NNMT gene" means the gene encoding NNMT protein. The base sequence of human NNMT gene and the amino acid sequence of human NNMT protein are known, for example, the base sequence of human NNMT gene and the amino acid sequence of human NNMT protein are registered by GenBank (GenBank Accession No. NM_006169.2), are published.

In this specification, human NNMT protein contains the protein consisting of the amino acids registered by GenBank, and the mutants occurred in the human individuals, and one or several amino acids are deleted, substituted and/or added in the protein consisting of the amino acid sequence registered by GenBank, wherein these proteins are occurred by polymorphism or mutation. But, these mutant human NNMT proteins have same functions as the protein consisting of the amino acids registered by GenBank.

In this specification, human NNMT gene contains the gene consisting of the base sequence registered by GenBank, and the variants occurred in the human individuals, for example, and one or several bases are deleted, substituted and/or added in the gene consisting of the base sequence registered by GenBank, wherein these genes are occurred by polymorphism or mutation. Furthermore, "NNMT gene" comprises variants consisting of base sequence having 80% or more for example 85% or more, 90% or more, 95% or more, 97% or more, 98% or more, 99% or more, 99.5% or more, 99.7% or more, or, 99.9% or more identity relative to the base sequence registered by GenBank. The identity of base sequence can be decided by using known algorithms of BLAST, FASTA etc. But, these variants encode the protein having same functions as the protein consisting of the amino acids registered by GenBank.

NNMT belongs to NNMT/PNMT/TEMT family. NNMT protein is the enzyme which catalyzes N-methylation of Nicotinamide, Pyridine, or other similar structure material. In the nicotinic acid metabolism system, it is known that the enzyme produces methyl nicotinamide and S-adenosyl homocysteine by transferring the methyl group of S-adenosylmethionine to nicotinamide (refer to Pharmacological reports 2009, 61, 76-85). The relationship between the amount of NNMT protein and chronic obstructive pulmonary disease is described in WO2012/123299, the relationship between the amount of NNMT protein and colon cancer is described in WO2004/071267, the treatment for obesity and metabolic disorders by inhibiting the enzymatic activity of NNMT is described in WO2012/068463. However, it is not known that the relationship between the enzymatic activity of NNMT or the change in NNMT gene expression and the treatment for chronic kidney disease.

In this specification, "a substance inhibiting the enzymatic activity of NNMT" means a substance inhibiting the enzymatic activity of NNMT which catalyzes N-methylation, and not particularly limited as long as such substances. An antibody and an antagonist against NNMT are exemplified as these substances.

In this specification, "COL1A1 gene" means the gene encoding COL1A1 protein. COL1A1 may also be referred to as Collagen1a1. The base sequence of human COL1A1 gene and the amino acid sequence of human COL1A1 protein are known, for example, the base sequence of human COL1A1 gene and the amino acid sequence of human COL1A1 protein are registered by GenBank (GenBank Accession No. NM_000088), are published. In this specification, human COL1A1 protein contains the protein consisting of the amino acids registered by GenBank, and the mutants occurred in the human individuals, and one or several amino acids are deleted, substituted and/or added in the protein consisting of the amino acid sequence registered by GenBank, wherein these proteins are occurred by polymorphism or mutation. But, these mutant human COL1A1 proteins have same functions as the protein consisting of the amino acids registered by GenBank.

In this specification, human COL1A1 gene contains the gene consisting of the base sequence registered by GenBank, and the variants occurred in the human individuals, for example, and one or several bases are deleted, substituted and/or added in the gene consisting of the base sequence registered by GenBank, wherein these genes are occurred by polymorphism or mutation.

As excessive accumulation of COL1A1 protein leads to fibrosis in the kidney, it is thought that effect of anti-fibrosis by suppressing COL1A1 gene or inhibiting COL1A1 protein expression leads to inhibiting the progression of chronic kidney disease (refer to American Journal of Pathology 2001, 159(4), 1313-1321).

In this specification, "COL3A1 gene" means the gene encoding COL1A1 protein. COL3A1 may also be referred to as Collagen3a1. The base sequence of human COL3A1 gene and the amino acid sequence of human COL3A1 protein are known, for example, the base sequence of human COL3A1 gene and the amino acid sequence of human COL3A1 protein are registered by GenBank (GenBank Accession No. NM_000090), are published. In this specification, human COL3A1 protein contains the protein consisting of the amino acids registered by GenBank, and the mutants occurred in the human individuals, and one or several amino acids are deleted, substituted and/or added in the protein consisting of the amino acid sequence registered by GenBank, wherein these proteins are occurred by polymorphism or mutation. But, these mutant human COL3A1 proteins have same functions as the protein consisting of the amino acids registered by GenBank.

In this specification, human COL3A1 gene contains the gene consisting of the base sequence registered by GenBank, and the variants occurred in the human individuals, for example, and one or several bases are deleted, substituted and/or added in the gene consisting of the base sequence registered by GenBank, wherein these genes are occurred by polymorphism or mutation.

As excessive accumulation of COL3A1 protein leads to fibrosis in the kidney, it is thought that effect of anti-fibrosis by suppressing COL3A1 gene or inhibiting COL1A1 protein expression leads to inhibiting the progression of chronic kidney disease (refer to Nephrol Dial Transplant 1997, 12, 1883-1889).

In this specification, "COL4A1 gene" means the gene encoding COL4A1 protein. COL4A1 may also be referred to as Collagen4a1. The base sequence of human COL4A1 gene and the amino acid sequence of human COL4A1 protein are known, for example, the base sequence of human COL4A1 gene and the amino acid sequence of human COL4A1 protein are registered by GenBank (GenBank Accession No. NM_001845), are published. In this specification, human COL4A1 protein contains the protein consisting of the amino acids registered by GenBank, and the mutants occurred in the human individuals, and one or several amino acids are deleted, substituted and/or added in the protein consisting of the amino acid sequence registered by GenBank, wherein these proteins are occurred by polymorphism or mutation. But, these mutant human COL4A1 proteins have same functions as the protein consisting of the amino acids registered by GenBank.

In this specification, human COL4A1 gene contains the gene consisting of the base sequence registered by GenBank, and the variants occurred in the human individuals, for example, and one or several bases are deleted, substituted and/or added in the gene consisting of the base sequence registered by GenBank, wherein these genes are occurred by polymorphism or mutation.

As excessive accumulation of COL4A1 protein leads to fibrosis in the kidney, it is thought that effect of anti-fibrosis by suppressing COL4A1 gene or inhibiting COL4A1 protein expression leads to inhibiting the progression of chronic kidney disease (refer to J Clin Lab Anal 1998, 12, 378-382).

In this specification, "a substance suppressing the gene expression" means a substance suppressing the mRNA transcription of the target gene, decomposing the transcribed mRNA or inhibiting the transcription of the mRNA and not particularly limited as long as such substances. A siRNA, an antisense oligonucleotide, a micro RNA, a ribozyme and an expression vector thereof are exemplified as these substances. In these substances, a siRNA or an antisense oligonucleotide and an expression vector thereof are preferred, a siRNA or an antisense oligonucleotide is more preferred. "A substance suppressing the gene expression" also contains a protein, a peptide and other small molecule other than above.

In this specification, "a siRNA" is an RNA molecule having a double-stranded RNA moiety consisting of about 15 to 40 bases, and the siRNA has a function of cleaving mRNA of a target gene having a sequence complementary to an antisense strand of said siRNA, and suppressing the target gene expression. In particular, the siRNA of the present invention is an RNA including a double-stranded RNA moiety consisting of a sense RNA strand consisting of a sequence homologous to a contiguous RNA sequence in mRNA of NNMT gene, and an antisense RNA strand consisting of a sequence complementary to the sense RNA sequence. The manufacturing and designing of the siRNA and a mutant siRNA to be below are within the scope of the ability of those skilled in the art.

The length of double-stranded of the RNA moiety is, as a base, about 15 to 40 bases, preferably 15 to 30 bases, more preferably 15 to 25 bases, still more preferably 18-23 bases, most preferably 19-21 bases. As to a terminal structure of a sense strand or antisense strand of siRNA, there is no particular limitation, and it can be appropriately selected depending on the purpose. For example, the terminal structure may be the one having a flush terminal or the one having protruding terminal (overhang), and the type with protruded 3'terminal is preferable.

A siRNA having an overhang consisting of several bases, preferably 1 to 3 bases, more preferably 2 bases, at 3' terminal of the sense RNA strand and the antisense RNA strand often has a great effect of suppressing a target gene expression, and is preferable. The type of bases of overhang is not particularly restricted, and the type may be either a base constituting a RNA or a base constituting a DNA.

Furthermore, it is also possible to use a siRNA in which is one to several nucleotides are deleted, substituted and/or added in either or both of the sense strand or antisense strand of the above-mentioned siRNA as a pharmaceutical composition for treating chronic kidney disease of the present invention. In this regard, the concept of one to several bases is not particularly limited, but it is preferably 1 to 4 bases, still preferably 1 to 3 bases, most preferably 1 to 2 bases. Specific example of the subject mutation include, without limitation, those in which the number of bases at the 3'-overhang moiety is from 0 to 3, those in which the base sequence of the 3'-overhang moiety is changed to another base sequence, those in which the length of the above-mentioned sense RNA strand and antisense RNA strand is different by 1 to 3 base due to the insertion, addition or deletion of bases, those in which the base in a sense strand and/or antisense strand is substituted with another base, and the like. However, it is necessary for the sense strand and antisense strand to be able to hybridize in these mutant siRNAs, and it is necessary for these mutant siRNA to have an ability to inhibit gene expression equivalent to siRNAs that do not have mutation.

Furthermore, the siRNA may be a siRNA in which one of the terminals has a molecule of a closed structure, such as a hairpin structure (Short Hairpin RNA; shRNA). The shRNA is a sense strand RNA of a specific sequence of a target gene, an antisense strand RNA consisting of a sequence complementary to the sense strand sequence, and a RNA including a linker sequence for connecting the both strands thereof, wherein the sense strand moiety and the antisense strand moiety hybridize to form a double-stranded RNA moiety.

The siRNA desirably does not exhibit a so-called off-target effect when clinically used. The off-target effect refers to an effect for suppressing the expression of another gene with partially homology to the siRNA used, other than the target gene. In order to avoid the off-target effect, it is possible to confirm that a candidate siRNA does not have cross reactivity using DNA microarray or the like in advance. Furthermore, it is possible to avoid the off-target effect by confirming as to whether there is a gene including a moiety having high homology with a sequence of a candidate siRNA, other than a target gene, using publicly known database provided by NCBI (National Center for Biotechnology Information) or the like.

In order to create the siRNA of the present invention, a publicly known method, such as a method by chemical synthesis and a method using a gene recombination technique, can be appropriately used. With a method by synthesis, a double-stranded RNA can be synthesized based on sequence information, using an ordinary method. In addition, in a method using a gene recombination technique, it is also possible to create such a siRNA by constructing an expression vector encoding a sense strand sequence and an antisense strand sequence and introducing the vector into a host cell, and then obtaining a sense strand RNA and an antisense strand RNA, each of which is produced by transcription. Furthermore, it is possible to create a desired double-stranded RNA by expressing a shRNA, which includes a sense strand of a specific sequence of a target gene, an antisense strand consisting of a sequence complementary to the sense strand sequence, and a linker sequence for connecting the both strands, and which forms a hairpin structure.

With regard to the siRNA, part of the nucleic acids constituting the siRNA may be a natural nucleic acid. With regard to the siRNA, all or part of the nucleic acids constituting the siRNA may be a modified nucleic acid so long as such a nucleic acid has an activity to suppress the expression of a target gene.

The modified nucleic acid means a nucleic acid in which modification is provided at a nucleoside (base moiety, sugar moiety) and/or an inter-nucleoside binding site, and that has a structure different from that of a natural nucleic acid. "Modified nucleoside", which constitutes a modified nucleic acid, includes, for example, abasic nucleoside; arabino-nucleoside, 2'-deoxyuridine, alpha-deoxyribonucleoside, beta-L-deoxyribonucleoside, nucleoside having other sugar modification; peptide nucleic acid (PNA), phosphate group-binding peptide nucleic acid (PHONA), locked nucleic acid (LNA), morpholino nucleic acid and the like. The above-mentioned nucleoside having sugar modification includes nucleosides having a substituted pentose, such as 2'-O-methylribose, 2'-deoxy-2'-fluororibose, 3'-O-methylribose, and the like; 1',2'-deoxyribose; arabinose; a substituted arabinose sugar; and a hexose, and sugar modification of an alpha-anomer. These nucleosides may be a modified base in which the base moiety is modified. Such modified bases include, for example, pyrimidine, such as 5-hydroxycytosine, 5-fluorouracil, 4-thiouracil, and the like; purine, such as 6-methyladenine, 6-thioguanosine, and the like; and other heterocyclic bases.

"Modified inter-nucleoside binding", which constitutes a modified nucleic acid, includes non-natural inter-nucleoside binding, such as alkyl linker, glyceryl linker, amino linker, poly(ethylene glycol) binding, inter-methyl phosphonate nucleoside binding; methylphosphonothioate, phosphotriester, phosphothiotriester, phosphorothioate, phosphorodithioate, triester prodrug, sulfone, sulfonamide, sulfamate, form acetal, N-methylhydroxylamine, carbonate, carbamate, morpholino, boranophosphonate, phosphoramidate and the like.

With regard to the nucleic acid sequence included in the double-stranded siRNA of the present invention, for example, the nucleic acid sequence described in SEQ ID No.2 may be used as the sense strand and the nucleic acid sequence described in SEQ ID No.3 may be used as the antisense strand.

The oligonucleotide sequence complementary to the mRNA of the target gene is called as "an antisense oligonucleotide", the antisense oligonucleotide inhibits the function of mRNA by forming double-stranded with the target gene (mRNA). "The antisense oligonucleotide" contains not only completely complementary oligonucleotide to the mRNA of the target gene, but also may contain some mismatching nucleotides, as long as such oligonucleotide can stably hybridize to mRNA.

In addition, such antisense oligonucleotide may be modified. After appropriate modification of such antisense oligonucleotide, the resulting modified antisense oligonucleotide will be degraded with difficulty in vivo, and suppresses the target gene expression more stably. Examples of such modified oligonucleotide include S-oligo type (phosphorothioate-type), C-5 thyazole type, D-oligo type (phosphodiester-type), M-oligo type (methylphosphonate-type), peptide nucleic acid type, phosphodiester binding type, C-5 propinyl pyrimidine type, 2-O-propylribose, and 2'-methoxyribose type antisense oligonucleotides. Moreover, such antisense oligonucleotide may also be an antisense oligonucleotide wherein at least some of the oxygen atoms composing phosphate groups are substituted with sulfur atoms or otherwise modified. Such antisense oligonucleotide is particularly excellent in terms of nuclease resistance and affinity for RNA. An example of an antisense oligonucleotide wherein at least some of the oxygen atoms composing phosphate groups are substituted with sulfur atoms or otherwise modified is an S-oligo type oligonucleotide.

Such antisense oligonucleotide (or a derivative thereof) can be synthesized by a standard method. For example, an antisense oligonucleotide or a derivative thereof can be easily synthesized using a commercially available DNA synthesizer (e.g., one produced by Applied Biosystems). It can be obtained by a synthesis method such as a solid-phase synthesis method using phosphoroamidite or a solid-phase synthesis method using hydrogen phosphonate.

With regard to the nucleic acid sequence included in the antisense oligonucleotide of the present invention, for example, the nucleic acid sequence described in SEQ ID No.4 or the nucleic acid sequence described in SEQ ID No. 5 may be used.

"A ribozyme" refers to an RNA having an enzyme activity to cleave an oligonucleotide. Since it has recently been shown that an oligo DNA having a base sequence of the enzyme activity site also possesses a nucleic acid cleavage activity, the term ribozyme is used in this specification as a concept encompassing DNA, as long as it possesses a sequence-specific nucleic acid cleavage activity. More specifically, the ribozyme can specifically cleave mRNA of the coding region of the target gene or an early transcript in the internal coding region of the mRNA (if the mRNA is an early transcript, an intron is included). The most versatile ribozymes are self-splicing RNAs found in infectious RNAs such as viroid and virusoid, and the hammerhead type, the hairpin type and the like are known. The hammerhead type exhibits enzyme activity with about 40 bases in length, and it is possible to specifically cleave the target mRNA alone by making several bases at both ends adjoining to the hammerhead structure portion (about 10 bases in total) to be a sequence complementary to the desired cleavage site of the mRNA. Furthermore, when the ribozyme is used in the form of an expression vector containing the DNA that encodes it, the ribozyme may be a hybrid ribozyme prepared by further joining a sequence modified from the tRNA to promote the migration of the transcription product to cytoplasm (Nucleic Acids Res., 2001, 29(13), 2780-2788).

A microRNA (referred to "miRNA") is a low molecular weight RNA, the microRNA has a function of regulating the gene expression by binding the complementary moiety of the target mRNA.

The substance suppressing the target gene expression may be a nucleic acid molecule such as a siRNA, an antisense oligonucleotide, a microRNA or ribozyme and may be an expression vector encoding the nucleic acid molecule. With regard to the expression vector, an oligonucleotide or polynucleotide encoding above nucleic acid molecule must be functionally bind with a promoter which may be active in the mammal cell which is administered. The used promoter is not particularly limited as long as such promoter may be active in the mammal which is administered, pol III promoter (for example, tRNA promoter, U6 promoter, H1 promoter), mammal promoter (for example, CMV promoter, CAG promoter, SV40 promoter) are exemplified as the used promoter.

The expression vector preferably contains a transcription termination signal, i.e., a terminator region, downstream of the oligo (poly) nucleotide encoding the nucleic acid molecule. Furthermore, the expression vector may further contain a selection marker gene for transformant cell selection (a gene that confers resistance to a drug such as tetracycline, ampicillin, or kanamycin, hygromycin, phosphinothricin, a gene that compensates for auxotrophic mutations, and the like).

Although the vector of the basic skelton which is used as the expression vector is not particularly limited, a plasmid vector and a virus vector are exemplified as the expression vector. The virus vector such as a retrovirus, an adenovirus, an adeno-associated virus, a herpes virus, a vaccinia virus, a poxvirus, a poliovirus, a sindbid virus and a sendai virus vector etc. are exemplified as the preferable vector which is administered to the mammal such as human.

Although the expression vector of the siRNA, the antisense oligonucleotide, the microRNA and the ribozyme are exemplified as the expression vector of the present invention, the expression vector of the siRNA or the antisense oligonucleotide is preferable in these vectors.

In the present invention, the substance inhibiting the enzymatic activity of NNMT or suppressing NNMT gene expression is used as an active ingredient of a pharmaceutical composition.

The pharmaceutical composition of the present invention may contain a single substance inhibiting the enzymatic activity of NNMT or suppressing NNMT gene expression as an active ingredient, may contain a plurality of substances as active ingredients. For examples, if the pharmaceutical composition of the present invention is the siRNA, single or more siRNA is uses as an active ingredient.

The target disease of the pharmaceutical composition of the present invention is chronic kidney disease, especially, chronic kidney disease with fibrosis.

Chronic kidney disease means the state in which "the observation of renal disease with positive proteinuria" or "reduced renal function (glomerular filtration rate less than 60 ml/min/1.73 m$^2$)" continues over three months, and chronic kidney disease includes chronic renal failure, chronic nephritis, tubulointerstitial failure, nephrotic syndrome, polycystic kidney disease, diabetic nephropathy, and renal sclerosis, etc.

Furthermore chronic kidney disease with fibrosis means chronic kidney disease displaying signs of fibrosis in glomerulosclerosis and tubulointerstitial etc.

The dosage form of the pharmaceutical composition of the present invention may be either of oral administration and parenteral administration.

These dosage forms can be formulated in accordance with a routine method, and may also include a carrier or an additive which is pharmaceutically acceptable. Examples of such carriers and additives include water, a pharmaceutically acceptable organic solvent, collagen, polyvinyl alcohol, polyvinylpyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum aragic, casein, agar, polyethylene glycol, diglycerol, glycerol, propylene glycol, vaseline, paraffin, stearyl alcohol, stearic acid, human serum albumin, mannitol, sorbitol, lactose, and a surface active agent which is acceptable as a medicinal additive.

The above-mentioned additive is selected either alone or in an appropriate combination from the above examples depending on the dosage form of the pharmaceutical composition of the present invention. In the case of oral administration, the dosage form may be tablets, capsules, subtle granules, powders, granules, liquid medicines, syrups or the like, or an adequate formulation can be administered.

In the case of parenteral administration, examples of the dosage form include pulmonary administration dosage forms (such as those using a nebulizer), nasal dosage forms, transdermal dosage forms (such as ointments, creams), injectable dosage forms, etc. In the case of the injectable dosage forms, for example, a drug can be administered systemically or locally through an intravenous injection, an intramuscular injection, an intraperitoneal injection, a subcutaneous injection, etc. such as an intravenous drip.

If the substance suppressing the target gene expression is the nucleic acid molecule such as the siRNA, the antisense oligonucleotide, the microRNA, the ribozyme or the expression vector encoding the nucleic acid molecule, the substance suppressing the target gene expression is introduced into a phospholipid vesicle, and the vesicle may be the pharmaceutical composition of the present invention.

The dose of the pharmaceutical composition of the present invention differs depending on age, sex, symptoms, the route of administration, the frequency of administration, the dosage form, renal function and liver function. The administration method is appropriately selected depending on the patient's age and symptoms. The effective administration dose per 1 kg weight at one time is from 0.01 µg to 1000 mg, is preferably from 0.1 µg to 100 µg. However, the dose of the pharmaceutical composition is not limited to these doses.

The present invention provides, in a further embodiment, (1) A method for treating chronic kidney disease, comprising a step of administering a substance inhibiting the enzymatic activity of NNMT or suppressing NNMT gene expression, (2) A method for treating chronic kidney disease with fibrosis, comprising a step of administering a substance inhibiting the enzymatic activity of NNMT or suppressing NNMT gene expression, (3) A substance inhibiting the enzymatic activity of NNMT or suppressing NNMT gene expression for treating chronic kidney disease, (4) A substance inhibiting the enzymatic activity of NNMT or suppressing NNMT gene expression for treating chronic kidney disease with fibrosis, (5) A use of a substance inhibiting the enzymatic activity of NNMT or suppressing NNMT gene expression for the production of therapeutic agent for treating chronic kidney disease, (6) A use of a substance inhibiting the enzymatic activity of NNMT or suppressing NNMT gene expression for the production of therapeutic agent for treating chronic kidney disease with fibrosis.

The present invention provides, in another embodiment, a method for screening a substance for treating chronic kidney disease, wherein the enzymatic activity of NNMT or NNMT gene expression is used as an indicator.

A test substance provided for the screening includes any known and novel compounds, and example thereof includes nucleic acids, carbohydrates, lipids, proteins, peptides, organic low molecular compounds, compound library prepared using the technology of combinatorial chemistry, random peptide library prepared by solid phase synthesis or phage display method or natural products derived from microorganisms, animals and plants, and marine organism.

The screening method of the present invention is a screening method for a therapeutic agent for chronic kidney disease, comprising (1) a step of contacting a substrate against NNMT protein with a test substance and with 1: a polypeptide comprising amino acid sequence described in SEQ ID No.1, or 2: a polypeptide comprising amino acid sequence that is one or several amino acids are deleted, substituted or added from the amino acid sequence described in SEQ ID No.1, and having the enzymatic activity of catalyzing N-methylation, and (2) a step of comparing the enzymatic activity of catalyzing N-methylation of the polypeptide when the test substance is contacted with the enzymatic activity of catalyzing N-methylation of the polypeptide when the test substance is not contacted, and (3) a step for selecting the test substance as a therapeutic agent for chronic kidney disease when the enzymatic activity of catalyzing N-methylation of the polypeptide when the test substance is contacted is decreased relative to the enzymatic activity of catalyzing N-methylation of the polypeptide when the test substance is not contacted.

Examples of the substrate against NNMT protein of the step (1) of the above method include nicotinamide or Pyridine etc. The polypeptide comprising amino acid sequence described in SEQ ID No.1 also contains a purified polypeptide and a polypeptide in the crushing solution of the cell or the tissue.

In the step (2) of the above method, the enzymatic activity of catalyzing N-methylation of the polypeptide is measured first. The measurement of the enzymatic activity can be performed by known methods with consideration of the kind of the used substrate. For example, when Nicotinamide is used as the substrate, Methyl nicotinamide levels produced from Nicotinamide is performed by known methods (refer to Journal of chromatography B, 2013, vol. 921-922, p. 87-95).

In the step (3) of the above method, the enzymatic activity of catalyzing N-methylation of the polypeptide when the test substance is contacted is compared with the enzymatic activity of catalyzing N-methylation of the polypeptide when the test substance is not contacted. The comparison of the enzymatic activity of catalyzing N-methylation of the polypeptide is preferably carried out on the basis of the presence or absence of a significant difference. The enzymatic activity of catalyzing N-methylation of the polypeptide when the test substance is not contacted may be acceptable both the enzymatic activity of catalyzing N-methylation of the polypeptide measured in advance and at the same time against measurement of the enzymatic activity of catalyzing N-methylation of the polypeptide when the test substance is contacted, but the enzymatic activity of catalyzing N-methylation of the polypeptide measured at the same time is preferable in terms of accuracy of the experiment or reproducibility.

In one embodiment, the screening method of the present invention is a screening method for a therapeutic agent for chronic kidney disease, comprising (1) a step of contacting a cell with a test substance, and (2) a step of comparing the enzymatic activity of NNMT in the cell when the test substance is contacted with the enzymatic activity of NNMT in a reference cell when the test substance is not contacted, and (3) a step for selecting the test substance as a therapeutic agent for chronic kidney disease when the enzymatic activity of NNMT in the cell when the test substance is contacted is decreased relative to the enzymatic activity of NNMT in the reference cell when the test substance is not contacted.

The cell of the step (1) of the above method refers to a cell permitting a measurement of the enzymatic activity of NNMT. In the step, the cell is contacted with the test substrate in the medium.

An animal cell such as a mammalian cell of a mouse, a rat, a hamster, a guinea pig, a rabbit, a dog, a monkey or a human can be used, a cell derived from a human, especially, a human renal tubular epithelial cell line HK2 cell or a human primary renal tubular epithelial cell and a kidney fibroblast is preferable as above cell.

A culture medium in which the cell is contacted with the test substance can be properly selectable depending on the kind of the used cell, but the examples of the culture medium include minimal essential medium (MEM) containing about 5 to 20% fetal bovine serum, Dulbecco's modified minimal essential medium (DMEM), PRMI1640 medium, 199 medium. A culture condition can also be properly selectable depending on the kind of the used cell, but for example, PH of the medium is about 6 to 8, culture temperature is generally about 30 to 40° C., culture time is about 12 to 144 hours.

In the step (2) of the above method, the enzymatic activity of NNMT in the cell when the test substance is contacted is measured first.

In the step (3) of the above method, the enzymatic activity of NNMT in the cell when the test substance is contacted is compared with the enzymatic activity of NNMT in the reference cell when the test substance is not contacted. The comparison of the enzymatic activity of NNMT is preferably carried out on the basis of the presence or absence of a significant difference. The enzymatic activity of NNMT in the reference cell when the test substance is not contacted may be acceptable both the enzymatic activity of NNMT in the reference cell measured in advance and at the same time against measurement of the enzymatic activity of NNMT in the cell when the test substance is contacted, but the enzymatic activity of NNMT in the reference cell measured at the same time is preferable in terms of accuracy of the experiment or reproducibility.

In one embodiment, the screening method of the present invention is a screening method for a therapeutic agent for chronic kidney disease, comprising (1) a step of contacting a cell with a test substance, and (2) a step of comparing NNMT gene expression level in the cell when the test substance is contacted with NNMT gene expression level in a reference cell when the test substance is not contacted, and (3) a step for selecting the test substance as a therapeutic agent for chronic kidney disease when NNMT gene expression level in the cell when the test substance is contacted is decreased relative to NNMT gene expression level in the reference cell when the test substance is not contacted.

The cell of the step (1) of the above method refers to a cell permitting a measurement of NNMT gene expression level. In the step, the cell is contacted with the test substrate in the medium.

The cell permitting a measurement of the expression of NNMT level refers to a cell enabling a direct or indirect evaluation of the expression level of a product, for example, transcription product or translation product, of NNMT gene. The cell enabling a direct evaluation of the expression level of a product of NNMT gene can be a cell capable of naturally expressing NNMT, whereas the cell enabling an indirect evaluation of the expression level of a product of NNMT gene can be a cell permitting a reporter assay of the transcriptional regulatory region of NNMT gene.

An animal cells such as a mammalian cell of a mouse, a rat, a hamster, a guinea pig, a rabbit, a dog, a monkey or a human can be used, cells derived from a human, especially, a human renal tubular epithelial cell line HK2 cells or a human primary renal tubular epithelial cells and a kidney fibroblast is preferable as a cell enabling a direct evaluation of the expression level of a product of the gene.

The cell permitting a reporter assay for the transcriptional regulatory region of the gene is a cell comprising the transcriptional regulatory region of the target gene and a reporter gene functionally joined to the region. The transcriptional regulatory region of the target gene and the reporter gene can be inserted into an expression vector. The transcriptional regulatory region of the target gene is not particularly limited, as far as the region is capable of controlling the expression of the target gene; examples include a region between the transcription initiation point and about 2 kbp upstream thereof, a region consisting of a base sequence resulting from deletion, substitution or addition of 1 or more bases in the base sequence of the region, and having the capability of controlling the transcription of the target gene, and the like. The reporter gene may be any gene that encodes an enzyme that catalyzes the production of a detectable protein or a detectable substance; examples include GFP (green fluorescence protein) gene, GUS (β-glucuronidase) gene, LUC (luciferase) gene, CAT (chloramphenicol acetyltransferase) gene and the like.

The cell inserted the transcriptional regulatory region of the target gene and the reporter gene functionally joined to the region is not particularly limited, as far as the transcriptional regulatory function of the target gene can be evaluated, namely the target gene expression level can be quantitatively analyzable.

In the step (2) of the above method, NNMT gene expression level in the cell when the test substance is contacted is measured first. The measurement of NNMT gene expression level can be performed by known methods with consideration of the kind of the used cell. For example, when a cell capable of naturally expressing NNMT is used as a cell permitting a measurement of NNMT gene expression level, the expression level can be measured by known methods on a gene product, for example, a transcription product or translation product. For example, the expression level of transcription product can be measured by RT-PCR, Northern blotting and the like using a total RNA prepared from the cells. The expression level of translation product can be measured by an immunological technique using an extract prepared from the cells. As the immunological technique, radioimmunoassay method (RIA method), ELISA method (refer to Methods in Enzymol. 1980, 70, 419-439), fluorescent antibody method and the like can be used. Meanwhile, when a cell permitting a reporter assay for the transcriptional regulatory region of NNMT gene is used as a cell permitting a measurement of NNMT gene expression level, the expression level can be measured on the basis of the signal intensity of the reporter.

In the step (3) of the above method, NNMT gene expression level in the cell when the test substance is contacted is compared with NNMT gene expression level in the reference cell when the test substance is not contacted. The comparison of NNMT gene expression level is preferably carried out on the basis of the presence or absence of a significant difference. The gene expression level in the reference cell when the test substance is not contacted may be acceptable both the gene expression level in the reference cell measured in advance and at the same time against measurement of the gene expression level in the cell when the test substance is contacted, but the gene expression level in the reference cell measured at the same time is preferable in terms of accuracy of the experiment or reproducibility.

In one embodiment, the screening method of the present invention is a screening method for a therapeutic agent for chronic kidney disease, comprising (1) a step of administering a test substance to a kidney disease pathological model animal (2) a step of comparing the enzymatic activity of NNMT in the animal when the test substance is administered with the enzymatic activity of NNMT in a reference animal when the test substance is not administered, and (3) a step for selecting the test substance as a therapeutic agent for chronic kidney disease when the enzymatic activity of NNMT in the animal when the test substance is administered is decreased relative to the enzymatic activity of NNMT in the reference animal when the test substance is not administered.

The kidney disease pathological model animal used by the step (1) of the above method means a non-human model animal obtained by referring to Kidney Int 2005, 68(3), 925-937 etc.

In one embodiment, the screening method of the present invention is a screening method for a therapeutic agent for chronic kidney disease, comprising (1) a step of administering a test substance to a kidney disease pathological model animal (2) a step of comparing NNMT gene expression level in the animal when the test substance is administered with NNMT gene expression level in a reference animal when the test substance is not administered, and (3) a step for selecting the test substance as a therapeutic agent for chronic kidney disease when NNMT gene expression level in the animal when the test substance is administered is decreased relative to NNMT gene expression level in the reference animal when the test substance is not administered.

The present invention is hereinafter described more specifically by means of the following Examples, by which, however, the invention is not limited in any way.

Example 1

Figure 1A:
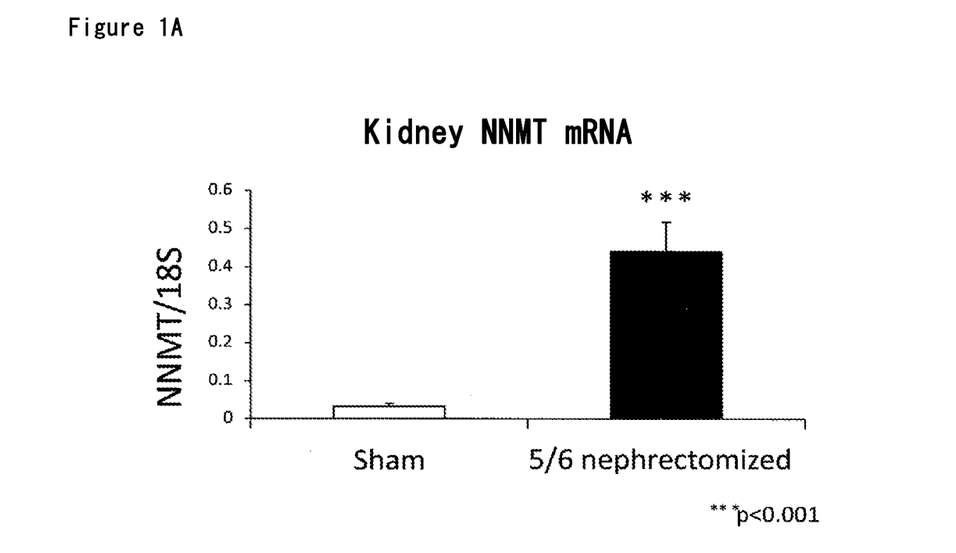
FIG. 1A shows the change of NNMT gene in 5/6 nephrectomized rats. The horizontal axis and the vertical axis indicate the experimental group and gene expression levels of NNMT (the relative ratio to expression level of housekeeping gene).
Figure 1B:
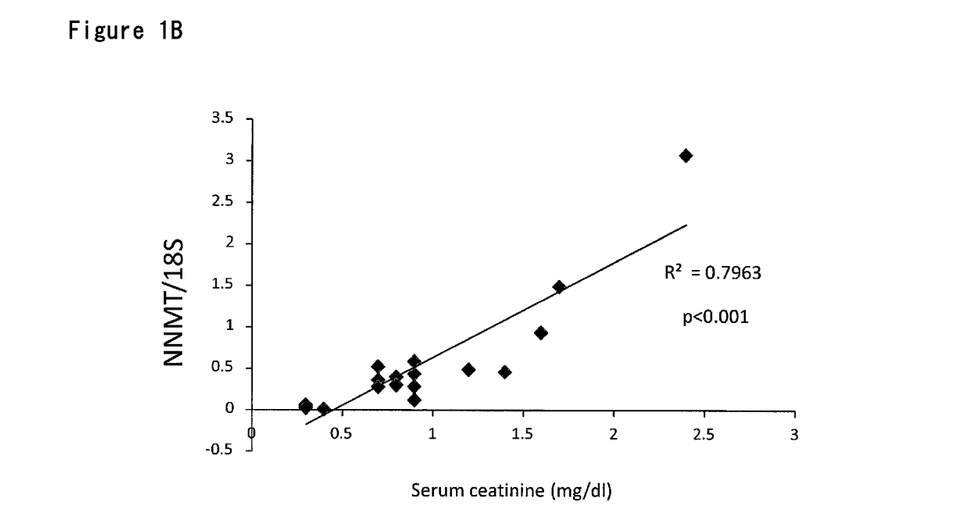
FIG. 1B shows a correlation between NNMT expression levels in kidney and creatinine values in serum. The horizontal axis and the vertical axis indicate creatinine values in serum and gene expression levels of NNMT (the relative ratio to expression level of housekeeping gene).

Using the 5/6 nephrectomy model (Refer to Kidney International., 1999, vol. 56, p. 898-909) which is an animal model of chronic kidney disease, we examined the presence of the metabolic abnormality of nicotinic acid in renal disease. The 5/6 nephrectomy model was prepared by operating to remove a kidney on male Sprague-Dawley rats (SD rat) of 6 weeks of age. In particular, after exposing the left renal from back under anesthesia with intraperitoneal injection of pentobarbital, ⅔ of left kidney was removed and the subcutaneous tissue and skin was sutured. After two weeks, the total right kidney was removed to complete a 5/6-nephrectomized model in the same manner. After 17 weeks from the completion of operation, samples for genetic analysis from kidney collected by dissection and serum samples were obtained. The quantitative PCR for total RNA extracted from the kidney was performed to compare the gene expression levels of NNMT between the control group performed sham operation and the 5/6-nephrectomized group. As a result, NNMT gene expression in kidney of the 5/6-nephrectomized group exhibited significant higher levels than that in kidney of the control group (FIG. 1A). NNMT expression levels showed positive correlation with serum creatinine levels (FIG. 1B), suggesting that abnormalities of nicotinic acid metabolism occurred in renal disease.

Example 2

Figure 2:
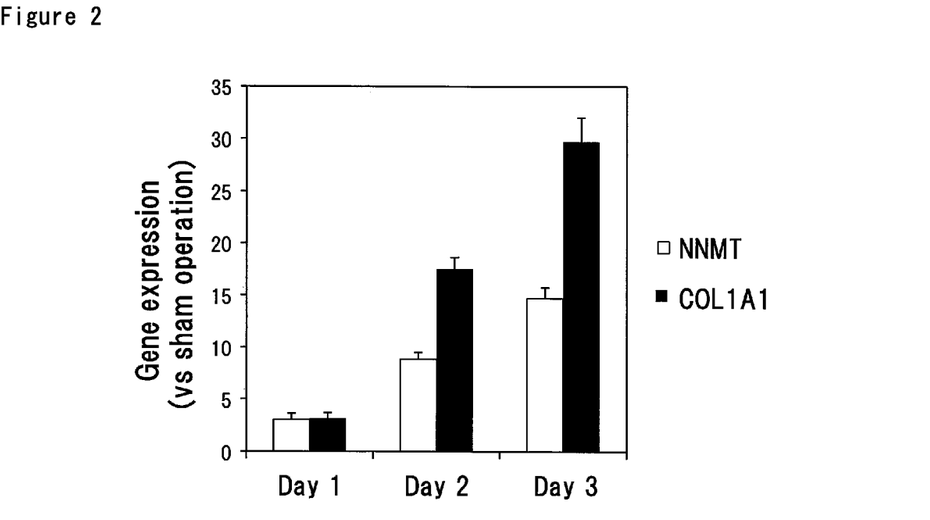
FIG. 2 shows the change of gene expression levels of NNMT and COL1A1 in UUO mice. The horizontal axis and the vertical axis indicate the number of days after ligation and the expression magnification for the sham-operated group.

The murine model of unilateral ureteral obstruction (hereinafter, also called UUO) is widely used in experiments of renal fibrosis as a model of renal fibrosis caused by hydronephrosis (Refer to Kidney International., 2005, vol. 68(3), p. 925-937). To evaluate the abnormalities of nicotinic acid metabolism in renal fibrosis, C57BL/6JJcl mice (male, 8 weeks-old, CLEA Japan Inc.) were subjected to UUO treatment to prepare a renal fibrosis model. In particular, after mice were anesthetized with isoflurane, the left ureter was exposed by a laparotomy for abdomen, ligated two places with surgical suture and then peritoneum and skin were stitched. Mice were dissected at 1 day, 2 days and 3 days after UUO treatment. In dissection, after laparotomy under anesthesia with somnopentyl, UUO-operated kidneys were collected to obtain sample for analysis of gene expression. Total RNA was extracted from kidney and the changes in gene expression levels of NNMT and COL1A1 were analyzed by quantitative PCR (FIG. 2). The expression levels of the UUO-operated group were compared with those of the sham-operated group prepared as the control group. As a result, the increased expression of NNMT gene in kidney was observed from 1 day after UUO treatment and the expression levels of COL1A1 gene was also confirmed to increase likewise.

Example 3

Figure 3A:
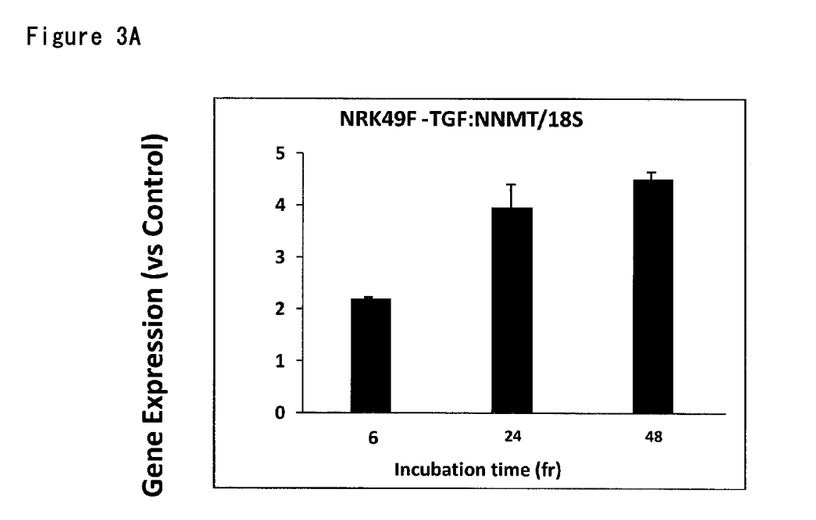
FIG. 3A shows the change of gene expression levels of NNMT in TGFβ1-stimulated rat kidney stromal fibroblasts (NRK49F). The horizontal axis and the vertical axis indicate stimulation time and the expression magnification for the control (unstimulated).
Figure 3B:
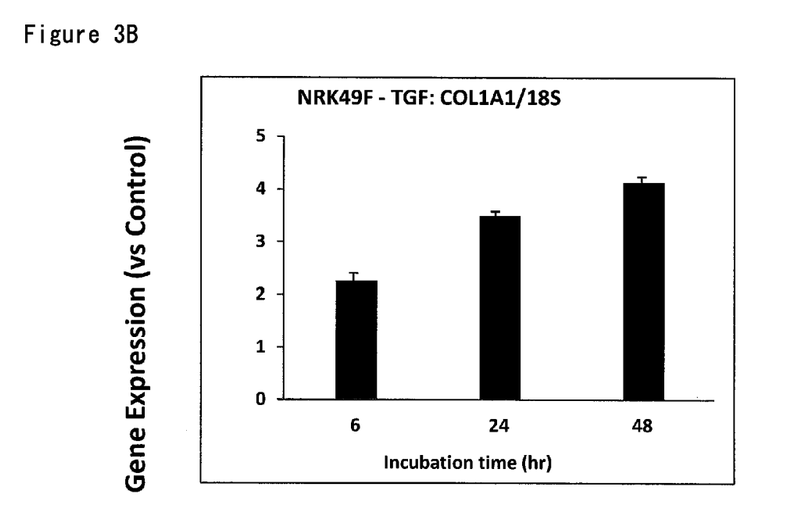
FIG. 3B shows the change of gene expression levels of COL1A1 in TGFβ1-stimulated rat kidney stromal fibroblasts (NRK49F). The horizontal axis and the vertical axis indicate stimulation time and the expression magnification for the control (unstimulated).
Figure 3C:
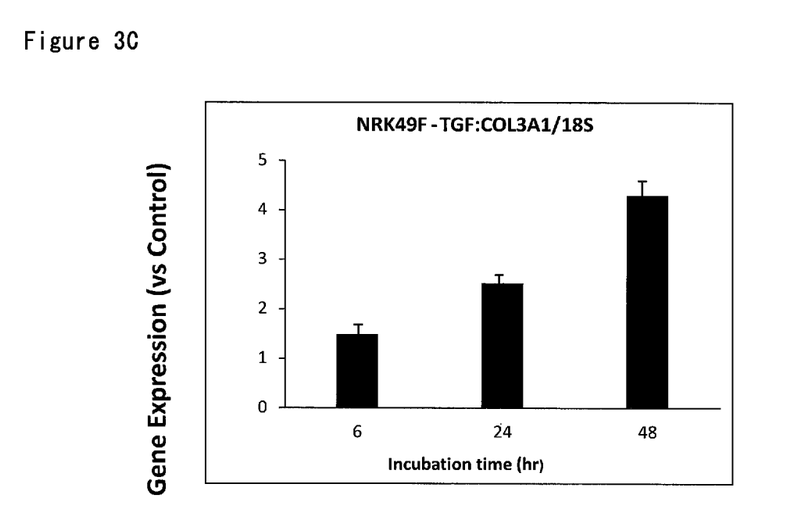
FIG. 3C shows the change of gene expression levels of COL3A1 in TGFβ1-stimulated rat kidney stromal fibroblasts (NRK49F). The horizontal axis and the vertical axis indicate stimulation time and the expression magnification of the control (unstimulated).
Figure 3D:
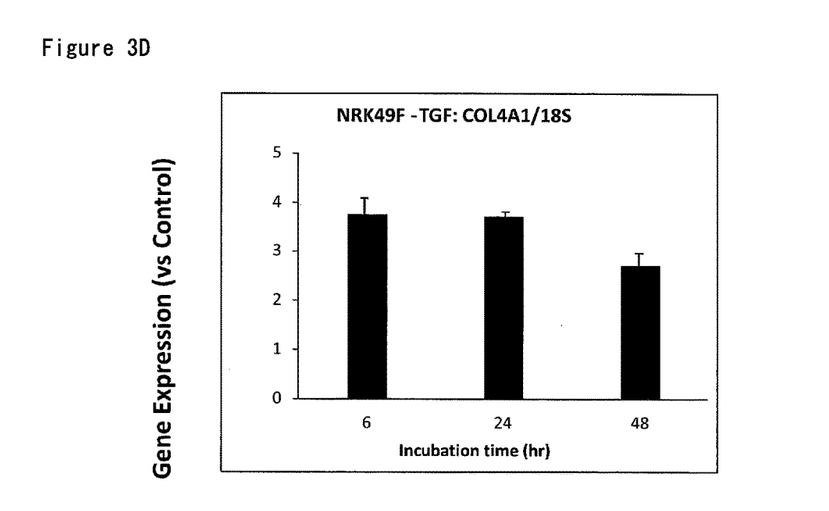
FIG. 3D shows the change of gene expression levels of COL4A1 in TGFβ1-stimulated rat kidney stromal fibroblasts (NRK49F). The horizontal axis and the vertical axis indicate stimulation time and the expression magnification for the control (unstimulated).

Effect of stimulation by TGFβ, known as a promoting factor of fibrosis (Refer to Nephrol Dial Transplant., 1998, vol. 13, p. 573-579), on gene expression of NNMT, COL1A1, COL3A1 and COL4A1 was examined using NRK49F cells that are rat kidney fibroblasts. NRK49F cells were seeded into 12 well plates at $4\times10^4$ cells/well/mL and culture medium was changed to serum-free medium after 72 hr. Recombinant human TGFβ1 (R & D Co., Ltd., 5 ng/mL) was added after 24 hr and the cells were cultured for 6, 24 and 48 hr. After culture, total RNA was extracted from cells and the gene expression levels of NNMT, COL1A1, COL3A1 and COL4A1 were analyzed by quantitative PCR. TGFβ1 stimulation resulted in time-dependent increases in gene expression levels of NNMT (FIG. 3A), COL1A1 (FIG. 3B) and COL3A1 (FIG. 3C). The gene expression of COL4A1 reached the maximum level in 6 hr and left the plateau to 24 hr (FIG. 3D). From these results, enhanced gene expression of NNMT was observed by TGFβ stimulation and gene expression of COL1A1, COL3A1 and COL4A1 was also confirmed to be enhanced likewise.

Example 4

Figure 4:
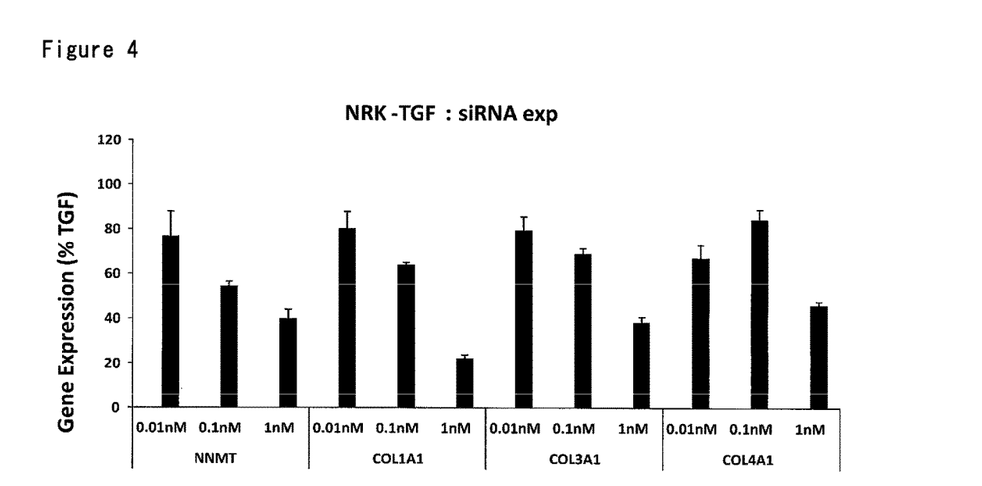
FIG. 4 shows the effect of siRNA treatment of NNMT on gene expression of collagen in TGFβ1-stimulated NRK49F cells. The horizontal axis indicates siRNA concentration of NNMT and expression gene. The vertical axis indicates the percentage of gene expression levels in TGFβ stimulation.

The siRNA of NNMT was introduced into NRK49F cells, rat kidney fibroblast cell line, the effect of which on enhanced gene expression of COL1A1, COL3A1 and COL4A1 by TGFβ stimulation was examined (FIG. 4). After NRK49F cells were seeded into 12 well plates at $4 \times 10^4$ cells/well/mL and culture for 72 hr, culture medium was changed to antibiotic-free medium and siRNA sequence (F; CCACAUCCAAUAAUGAAGGACUCUU (SEQ ID NO: 2), R; AAGAGUCCUUCAUUAUUGGAUGUGG (SEQ ID NO: 3)) for rat NNMT purchased was introduced into cells for 24 hr by lipofection method using RNAiMAX (Invitrogen Corp.) which is an introduction reagent of siRNA. Next, culture medium was changed to serum-free medium and after 24 hr, human recombinant TGFβ (R & D Co., Ltd., 5 ng/mL) was added and cultured for 48 hr. After culture, total RNA was extracted from cells and the gene expression levels of NNMT, COL1A1, COL3A1 and COL4A1 were analyzed by quantitative PCR. TGFβ1 stimulation resulted in about 3.6-fold increase in gene expression of NNMT, while siRNA treatment at 0.01, 0.1 and 1 nM knocked down 23, 45 and 60% of gene expression of NNMT, respectively. Likewise, TGFβ1 stimulation showed 7.1, 6.5 and 3.1-fold increases in gene expression of COL1A1, COL3A1 and COL4A1, respectively, while siRNA treatment at 0.01, 0.1 and 1 nM induced 20, 36 and 78% decreases in gene expression of COL1A1, 20, 31 and 62% decreases in that of COL3A1, and 33, 15 and 57% decreases in that of COL4A1, respectively. From these results, the contribution of NNMT for enhanced gene expression of COL1A1, COL3A1 and COL4A1 was confirmed, suggesting that fibrosis is attenuated by NNMT inhibition.

Example 5

Figure 5:
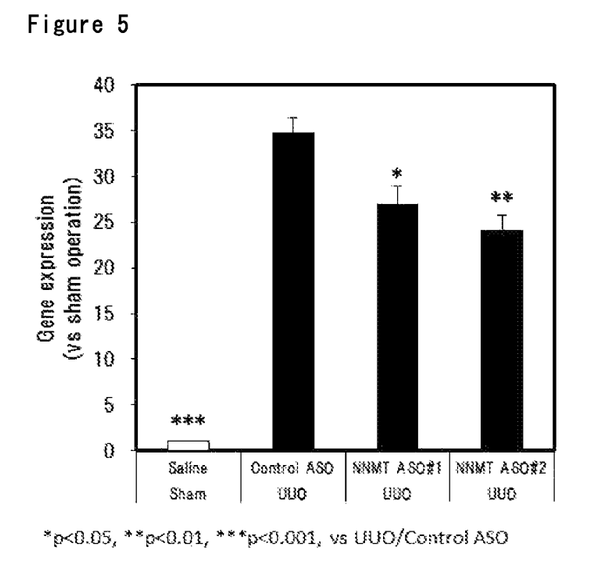
FIG. 5 shows the change of gene expression levels of COL1A1 with ASO administration in unilateral ureteral obstruction in mice. The horizontal axis and the vertical axis indicate the experimental group and the expression magnification for the sham-operated group.

Administration test of antisense nucleotide (ASO) to UUO mice was carried out (FIG. 5). In particular, the ASO (#1: CACAGTGTCTGGAC (SEQ ID NO: 4), #2: GTGGTAGAAGAGTA (SEQ ID NO: 5)) was subcutaneously administered to C57BL/6JJcl mouse (male, 8 weeks old, CLEA Japan Inc.) at 15 mg/kg and after 2 days, mice was subjected to UUO treatment. Mice were dissected under anesthesia with somnopentyl at 4 days after UUO treatment and UUO-operated kidneys were collected to obtain sample for analysis of gene expression. Total RNA was extracted from the kidneys and the gene expression levels of NNMT, COL1A1 were analyzed by quantitative PCR. The gene expression level of the NNMT ASO treated group was compared with that of the control ASO treated group prepared as the control group. As a result, a significant inhibition for gene expression of COL1A1 was observed in the NNMT ASO-treated group compared with the control ASO-treated group.

The present invention is useful for developing or manufacturing of a pharmaceutical composition for treating chronic kidney disease, especially for treating chronic kidney disease with fibrosis.

The invention claimed is:

1. A method of treatment comprising a step of administering a substance inhibiting the enzymatic activity of nicotinamide N-methyltransferase (NNMT) or suppressing NNMT gene expression for treating chronic kidney disease.

2. The method of claim 1, wherein the substance inhibiting the enzymatic activity of NNMT or suppressing NNMT gene expression is a nucleic acid.

3. The method of claim 2, wherein the nucleic acid is a siRNA, an antisense oligonucleotide or an expression vector thereof.

* * * * *